US00PP36833P2

(12) United States Plant Patent
Kerley et al.

(10) Patent No.: US PP36,833 P2
(45) Date of Patent: Jul. 22, 2025

(54) ***PRIMULA* PLANT NAMED 'KERBELROSA'**

(50) Latin Name: *Primula elatior*
Varietal Denomination: KERBELROSA

(71) Applicant: Kerley & Co, Willingham (GB)

(72) Inventors: David William Kerley, Over (GB); Timothy Edward Kerley, Willingham (GB)

(73) Assignee: Kerley & Co. Ltd. (GB)

( * ) Notice: Subject to any disclaimer, the term of this patent is extended or adjusted under 35 U.S.C. 154(b) by 0 days.

Patent file contains an affidavit/declaration under 37 CFR 1.130(b).

(21) Appl. No.: 18/799,782

(22) Filed: Aug. 9, 2024

(51) Int. Cl.
*A01H 5/02* (2018.01)
*A01H 6/00* (2018.01)

(52) U.S. Cl.
USPC ..... Plt./472

(58) Field of Classification Search
USPC ..... Plt./472
See application file for complete search history.

(56) References Cited

PUBLICATIONS https://plantago.nl/plantindex/plant/BO/P/1/primula-vulgaris-kerbelrosa/412861.html. Retrieved from the Internet on Nov. 13, 2024.*
https://fermer-ru.translate.goog/blog/19352/sz-cherenkov-georgin-pelargoniy-lukovic-liliy-na-vesnu-2017-278340?page=2640&destination=node. Retrieved from the Internet on Nov. 13, 2024. (Referenced as "SZ Vegetatives" in the action).*

* cited by examiner

*Primary Examiner* — Susan McCormick Ewoldt
(74) *Attorney, Agent, or Firm* — Cassandra Bright

(57) ABSTRACT

A new and distinct cultivar of *Primula* plant named 'KERBELROSA' is described, characterized by abundant, fully-double rose-colored flowers with a silver rim. Plants have compact, uniform habits. The new variety is a *Primula*, normally used as an ornamental garden or landscape plant.

2 Drawing Sheets

Figure 1:
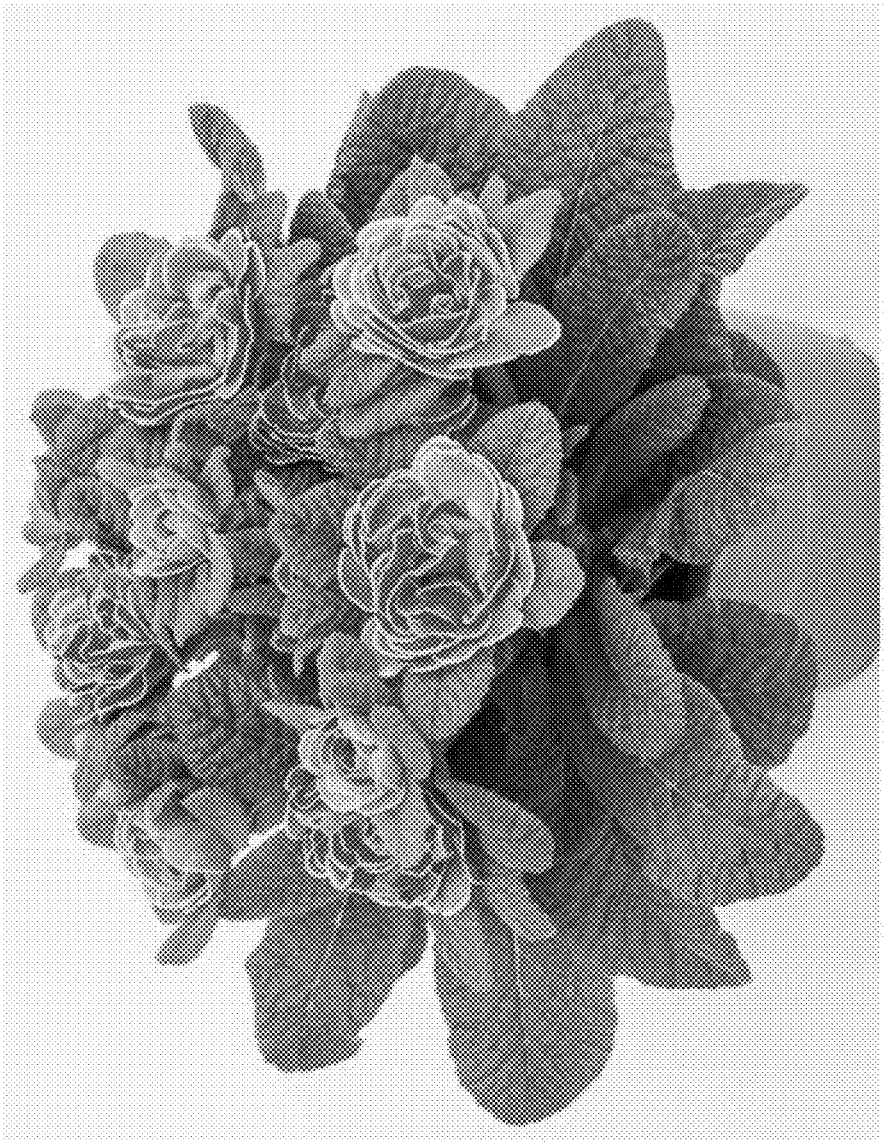

Latin name of the genus and species: *Primula elatior.*
Variety denomination: 'KERBELROSA'.

BACKGROUND OF THE INVENTION

The new cultivar is the product of a planned breeding program under the direction of the inventors. *Primula* 'KERBELROSA' resulted from the crossing of the seed parent, an unpatented, unnamed, proprietary variety of *Primula*, and the pollen parent, a different unnamed, unpatented, proprietary variety of *Primula*. The crossing resulting in the new variety was made in April of 2017 at a research greenhouse in Cambridge, United Kingdom. Selection of the new variety 'KERBELROSA' was made in March of 2018, by the inventor at a research greenhouse located in Cambridge, United Kingdom.

Asexual reproduction of the new cultivar 'KERBELROSA' was first performed in Cambridge the United Kingdom during May of 2018, by tissue culture. This and subsequent propagation has shown that the unique features of this cultivar are stable and reproduced true to type in successive generations.

SUMMARY OF THE INVENTION

The cultivar 'KERBELROSA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KERBELROSA'. These characteristics in combination distinguish 'KERBELROSA' as a new and distinct *Primula* cultivar:

1. Large, double flowers.
2. Deep rose flower color with a silver rim.
3. Abundant flowering.
4. Compact plant habit.
5. Enlarged calyx framing each flower.

PARENT COMPARISONS

Plants of the new cultivar 'KERBELROSA' are similar to plants of the seed parent, in most horticultural characteristics. However, plants of the new cultivar differ in the following ways:

1. Flowers of the new variety are double, while flowers of the seed parent are single.
2. Flowers of the new variety are sterile, while flowers of the seed parent are fertile.

Plants of the new cultivar 'KERBELROSA' are similar to plants of the pollen parent, in most horticultural characteristics. However, plants of the new cultivar differ in the following ways:

1. Flowers of the new variety are double, while flowers of the pollen parent are single.
2. Flowers of the new variety are sterile, while flowers of the pollen parent are fertile.

COMMERCIAL COMPARISONS

Plants of the new variety can be compared to plants of the *Primula* cultivar 'Belarina Pink Ice', unpatented. Plants of the new *Primula* differed from plants of the cultivar 'Belarina Pink Ice' in the following characteristics:

1. Flowers of the new variety are larger than flowers of this comparator.
2. Calyx of the new variety is approximately 30 to 50% larger than the calyx of this comparator.
3. Flower color of the new variety is rose with a silver rim, while the flower color of this comparator is light pink on white with no silver rim.

Plants of the new variety can be compared to plants of the *Primula* cultivar 'Belarina Pink Champagne', unpatented. Plants of the new *Primula* differed from plants of the cultivar 'Belarina Pink Champagne' in the following characteristics:

1. Flowers of the new variety are larger than flowers of this comparator.
2. Calyx of the new variety is larger than the calyx of this comparator.
3. Flower color of the new variety is rose with a silver rim, while the flower color of this comparator is light pink on cream with no silver rim.

BRIEF DESCRIPTION OF THE PHOTOGRAPHS

The accompanying photograph in FIG. 1 illustrates in full color a typical plant of 'KERBELROSA' grown in Over, Cambridge, United Kingdom, in a glass-covered greenhouse. This plant was about 7 months old when the photographs were taken. During the production of the plants, day temperatures ranged from 5° to 15° C. and night temperatures ranged from 2° to 12° C.

Figure 2:
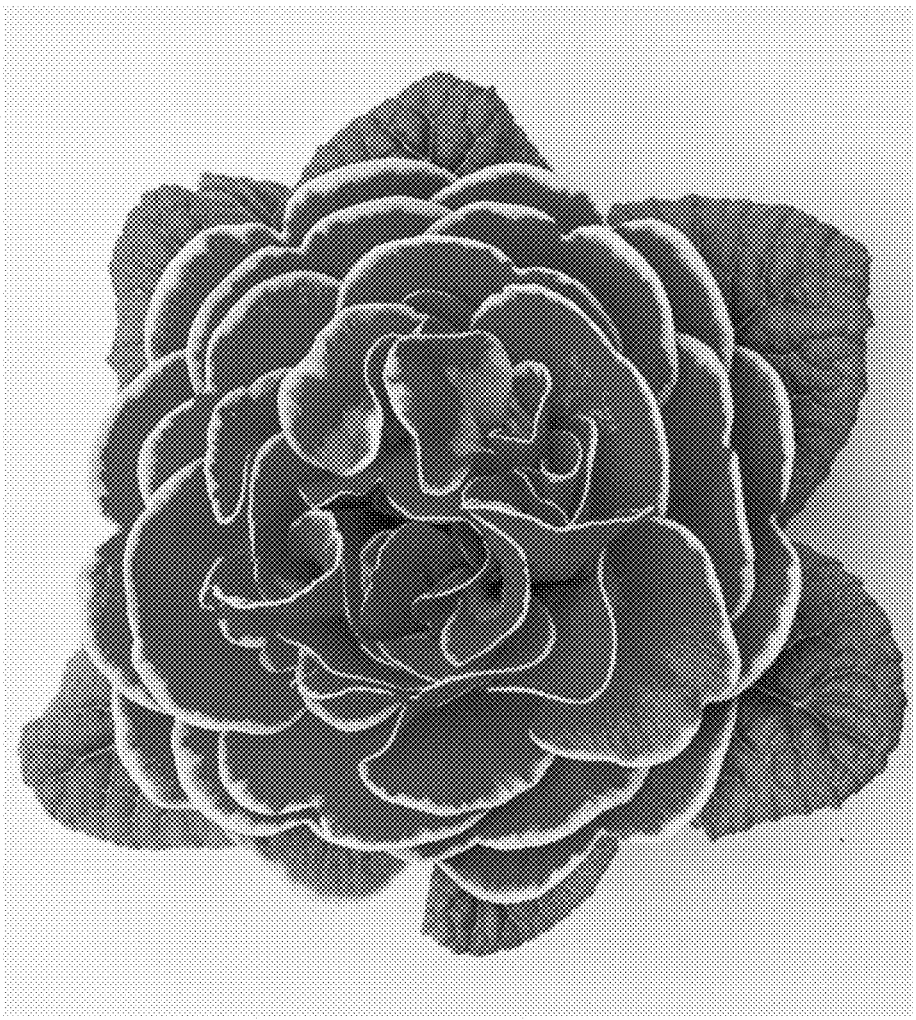

FIG. 2 illustrates a close up of a typical flower of 'KERBELROSA'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart, 2015 except where general terms of ordinary dictionary significance are used. The following observations and measurements describe 'KERBELROSA' plants grown in a greenhouse in Cambridge, United Kingdom. During the production of the plants, day temperatures ranged from 1.5° C. to 25° C. and night temperatures ranged from 1.5° C. to 15° C. No chemical or photoperiodic treatments were given. Measurements were taken during Spring and numerical values represent averages of typical flowering types.

Botanical classification: *Primula elatior* 'KERBELROSA'.

PROPAGATION

Method: Tissue culture.

Time to produce a rooted plant: About 6 weeks at 20° C.

Root description: Fibrous, freely branching, colored near RHS White 155A.

PLANT

Plant form/habit: Upright, compact and uniform; mounding.

Height: 12.5 cm.

Plant spread: 22 cm.

Branching characteristics: No branches, foliage emerges basally.

Vigor: Vigorous. Approximately 20 weeks from potting a rooted liner to flowering in a 1 liter pot during winter conditions in the UK.

FOLIAGE

Leaf:

*Arrangement*.—Basal, simple.
*Length*.—11.2 cm.
*Width*.—6.3 cm.
*Shape*.—Oblanceolate.
*Apex*.—Obtuse, rounded.
*Base*.—Sessile.
*Margin*.—Crenate, undulating.
*Texture of top surface*.—Rugose.
*Texture of bottom surface*.—Rugose with prominent venation.
*Color*.—Developing foliage upper side: RHS Green 137A. Developing foliage under side: RHS Yellow-Green 146B. Mature foliage upper side: RHS Green NN137B. Mature foliage under side: RHS Yellow-Green 146A.
*Venation*.—Type: Pinnate. Venation color upper side: RHS Yellow-Green N148B. Venation color under side: RHS Yellow-Green N148D.

Petiole:

*Length*.—1.1 cm.
*Diameter*.—0.75 cm.
*Color*.—Upper Surface: RHS Yellow-Green 196A with slight blush of Red 184B. Lower Surface: RHS Yellow-Green 196B with slight blush of Red 184C.
*Texture upper surfaces*.—Glabrous.
*Texture lower surfaces*.—Glabrous.

FLOWER

Bloom period: Recurrent flowering during the Spring under United Kingdom outdoor conditions.

Flower type/habit: Solitary, rounded double flowers facing upright and outward. Each flower framed by enlarged calyx.

Persistence: Persistent.

Fragrance: None.

Flowers per inflorescence: 40 to 50 flowers and buds per plant.

Flower bud:

*Height*.—1.4 cm.
*Diameter*.—1.2 cm.
*Shape*.—Conical.
*Color*.—RHS Yellow-Green 144B.
*Texture*.—Generally glabrous. Slight pubescence along central vein of sepals.

Individual flower:

*Diameter*.—5 cm.
*Depth*.—2.5 cm.

Petals:

*Quantity*.—48 to 60 per flower, in several concentric whorls.
*Length* (*including tube*).—2.4 cm.
*Width*.—1.9 cm.
*Shape*.—Obcordate.
*Apex*.—Emarginate.
*Margin*.—Entire, slightly undulating.
*Texture, upper and lower surfaces*.—Glabrous.
*Longevity*.—10 to 11 days.

*Color*.—Developing petals, upper surface: RHS Purple-Pink 73B with an eye at base of Yellow 7A surrounded by a band of Yellow 8D. Margin has a small rim of White NN155C, wider rim on outer petals. Developing petals, lower surface: RHS Purple-Pink 73B with an eye of Yellow-Green 144C at base surrounded by a band of Yellow 4D. Mature petals, upper surface: RHS Purple-Pink 73A. with, a small eye at base of Yellow 12A with a hint of Yellow 17A, surrounded by a band of White NN155D. Margin has a thin rim of White NN155D, wider on outer petals. Mature petals, lower surface: RHS Purple-Pink 73A with a small eye at base of Yellow 3B fading to Yellow 8D.

Flower throat:

*Diameter*.—0.5 cm.

*Texture*.—Glabrous.

*Color*.—RHS Yellow 8C.

Flower tube:

*Diameter*.—0.3 cm.

*Texture*.—Glabrous.

*Color*.—RHS Yellow 1D.

Calyx:

*Depth*.—3.5 cm.

*Diameter*.—6 cm.

Sepals:

*Quantity*.—5 in a single whorl; fused at base.

*Length*.—3.9 cm.

*Width*.—2.4 cm.

*Shape*.—Oblanceolate.

*Apex*.—Obtuse.

*Margin*.—Entire.

*Texture upper surface*.—Slightly rugose.

*Texture lower surface*.—Rugose, prominent venation.

*Color, upper surface*.—RHS Yellow-Green 144A.

*Color, lower surface*.—RHS Yellow-Green 146A.

Peduncle:

*Length*.—8.7 cm.

*Diameter*.—0.3 cm.

*Orientation*.—Upright and outwards.

*Strength*.—Strong.

*Color*.—RHS Yellow-Green 145A, with faint blush of Purple-Red 184D near the flower.

*Texture*.—Slightly pubescent.

REPRODUCTIVE ORGANS

Development of reproductive organs has not been observed.

OTHER CHARACTERISTICS

Disease resistance: Plants of the new *Primula* have not been noted to be resistant nor susceptible to pathogens and pests common to *Primula*.

Temperature tolerance: Plants of the new *Primula* have been observed to have tolerated temperatures from about −5° to 28° C.

Fruit/seed production: Fruit and seed production not observed; flowers are sterile.

What is claimed is:

1. A new and distinct cultivar of *Primula* plant named 'KERBELROSA' as herein illustrated and described.

* * * * *